United States Patent
Woodroof et al.

(10) Patent No.: US 9,155,820 B2
(45) Date of Patent: Oct. 13, 2015

(54) SKIN SUBSTITUTE MANUFACTURING METHOD

(75) Inventors: E. Aubrey Woodroof, Carlsbad, CA (US); Mitchell Enright, Carlsbad, CA (US)

(73) Assignee: AUBERGINE MEDICAL, LLC, Bannockburn, IL (US)

( * ) Notice: Subject to any disclaimer, the term of this patent is extended or adjusted under 35 U.S.C. 154(b) by 410 days.

(21) Appl. No.: 12/558,563

(22) Filed: Sep. 13, 2009

(65) Prior Publication Data

US 2010/0000676 A1    Jan. 7, 2010

Related U.S. Application Data

(63) Continuation of application No. 12/326,373, filed on Dec. 2, 2008, now Pat. No. 7,815,931, which is a continuation-in-part of application No. 12/049,321, filed on Mar. 5, 2008, now abandoned.

(51) Int. Cl.
*A61F 2/10* (2006.01)
*A61L 27/60* (2006.01)

(52) U.S. Cl.
CPC ..................................... *A61L 27/60* (2013.01)

(58) Field of Classification Search
CPC ....................................................... A61L 27/60
USPC ....................................................... 425/84, 85
See application file for complete search history.

(56) References Cited

U.S. PATENT DOCUMENTS

| | | | | |
|---|---|---|---|---|
| 4,049,863 A * | 9/1977 | Vassiliou | | 428/324 |
| 5,156,856 A * | 10/1992 | Iwasaki et al. | | 425/85 |
| 6,013,215 A * | 1/2000 | Iwamoto et al. | | 264/87 |
| 6,024,003 A * | 2/2000 | Newman et al. | | 83/24 |
| 2003/0081979 A1 * | 5/2003 | Garcia et al. | | 400/627 |

* cited by examiner

*Primary Examiner* — Galen Hauth
(74) *Attorney, Agent, or Firm* — Hultquist, PLLC; Steven J. Hultquist

(57) ABSTRACT

An improved skin substitute production method is presented that minimizes destruction of the nylon weave netting that comprises the skin substitute at the pore holes of the skin substitute membrane, The skin substitute is comprised of non-biological materials produced with a series of regularly-spaced pores and a nylon weave netting. The top component is a thin (approximately 0.001" thick) silicone elastomer in which pore holes have been vacuum-pulled; physically attached to the silicone elastomer is a fine knitted nylon fabric (12/1, 15/1 denier).

13 Claims, 2 Drawing Sheets

SKIN SUBSTITUTE MANUFACTURING METHOD

RELATED APPLICATIONS

This is a Continuation-in-Part of U.S. patent application Ser. No. 12/326,373, now U.S. Pat. No. 7,815,931, which is a Continuation-In-Part of U.S. patent application Ser. No. 12/049,321, now abandoned.

FIELD OF THE INVENTION

This invention relates to the field of artificial skin substitutes used for wound and burn dressings, and other purposes.

BACKGROUND OF THE INVENTION

A number of skin substitutes exist in the current market that address the wound dressing and burn dressing problem. There is currently no perfect product and there are still gaps in the capabilities of state-of-the-art artificial skin substitutes.

The present invention provides a precision, porous, stretchable membrane that fosters an ideal three-dimensional environment for the protection of existing cells and growth of new skin cells. The present invention promotes rapid adhesion to the wound as well as large sheet coverage (up to 24" by 24"), not offered by the state-of-the-art.

The present invention is made stretchable and tear resistant by using a fine knit nylon fabric. Additionally, the porosity of the overlying membrane is greater in terms of placement and area of pores, compared to the state-of-the-art. The membrane is semi-permeable, allowing water vapor transmission and preventing fluid accumulation between the dressing and the wound surface.

As a consequence, the porosity of the membrane enhances the healing process, making it faster and safer. The three-dimensional membrane structure is also made capable of holding a biological agent that further increases the healing abilities of the covered area. These agents include biological agents such as chondrotin 6 sulfate, and others.

The present invention is easy to handle, flexible and stretchable, can be stored at room temperature, and is safe and sterile. Packaging and sterilizing of the invention is crucial. From a production and laboratory standpoint, manufacturing the invention is efficient in terms of time and materials. After manufacture, the product will be ready for immediate sterilization and shipping for use on patients.

TECHNICAL BACKGROUND

Some ideal properties of a skin substitute from (Rusczak, 2006) and Properties from (Robert H. Demling)
a. Rapid and sustained adherence to wound surface and Inner surface structure that permits cell migration, proliferation and in growth of new tissue
(The most important criterion is adherence)
b. Absence of antigenicity
c. Tissue compatible
d. Absence of local or systemic toxicity
e. Impermeable to exogenous microorganisms
f. Water vapor transmission similar to normal skin
g. Rapid and sustained adherence to wound surface
h. Conformal to surface irregularities
i. Elastic to permit motion of underlying tissue
j. Resistant to linear and shear stresses
k. Tensile strength to resist fragmentation (when removed)
l. Inhibition of wound surface flora and bacteria
m. Long shelf life, minimal storage requirements
n. Low cost
o. Minimize nursing care of wound
p. Minimize patient discomfort
q. Translucent properties to allow direct observation of healing
r. Reduce heal-time
s. Patient acceptance

PRIOR ART

Tissue Based Skin Substitutes

Alloderm by LifeCell, Inc—AlloDerm is human tissue and is processed from donated human skin. The tissue goes through a cell removal process while retaining the important biochemical and structural components. AlloDerm is, thus, acellular human dermis. U.S. Pat. No. 6,933,326—Particulate acellular tissue matrix.

Apligraf by Organogenesis Inc.—Apligraf is supplied as a living, bi-layered skin substitute: the epidermal layer is formed by human keratinocytes and has a well-differentiated stratum corneum; the dermal layer is composed of human fibroblasts in a bovine Type I collagen lattice. U.S. Pat. Nos. 4,485,096 5,106,949 4,536,656

Dermagraft by Smith & Nephew Inc—Dermagraft is a cryopreserved human fibroblast-derived dermal substitute; it is composed of fibroblasts, extracellular matrix, and a bioabsorbable scaffold. U.S. Pat. No. 4,963,489: Three-dimensional cell and tissue culture system Epicel by GenzymeBiosurgery—Epicel grafts are sheets of skin cells ranging from 2 to 8 cell layers thick. The grafts are grown or cultured from a postage stamp sized sample of patient's own healthy skin, which is sent to GenzymeBiosurgery for processing. The cells within the epidermis of the skin sample are separated and grown by a process called "tissue culture", which involves feeding the cells with specific nutrients and maintaining strict climate controls so that the cells multiply to form sheets of skin. During this process, irradiated mouse cells, also referred to as 3T3 cells, are used to promote cell growth and to ensure that there will be a sufficient number of grafts available as soon as possible for treatment. U.S. Pat. No. 6,964,869: Method and composition for skin grafts.

EZ Derm by Brennen Medical, Inc—A modified pigskin impregnated with a soluble silver compound intended for treatment of burns. Originally developed by Genetic Laboratories. U.S. Pat. No. 6,923,990 Stabilized silver-ion amine complex compositions and methods. This is not a patent for EZ Derm but it is related to the silver that EZ-Derm uses OrCel by Ortec International Inc.—A bilayered cellular matrix in which normal human allogeneic skin cells (epidermal keratinocytes and dermal fibroblasts) are cultured in two separate layers into a Type I bovine collagen sponge. Donor dermal fibroblasts are cultured on and within the porous sponge side of the collagen matrix while keratinocytes, from the same donor, are cultured on the coated, non-porous side of the collagen matrix.

TransCyte by Smith and Nephew, Inc—Consists of a polymer membrane and newborn human fibroblast cells cultured under aseptic conditions in vitro on a nylon weave. Prior to cell growth, this nylon weave is coated with porcine dermal collagen and bonded to a polymer membrane (silicone). This membrane provides a transparent synthetic epidermis when the product is applied to the burn.

As fibroblasts proliferate within the nylon weave during the manufacturing process, they secrete human dermal collagen, matrix proteins and growth factors. Following freezing, no cellular metabolic activity remains; however, the tissue matrix and bound growth factors are left intact. The human fibroblast-derived temporary skin substitute provides a temporary protective barrier. TransCyte is transparent and allows direct visual monitoring of the wound bed.

Silver Based Skin Substitutes

Aquacell Ag

Silver powered antimicrobial dressing

ActiCoat

Using unique silver technology:

SILCRYST Nanocrystalline

Other Synthetic/Similar to our membrane Skin Substitutes

Biobrane, Biobrane-L by Bertek Pharmaceuticals—Biobrane/—E is a biocomposite temporary wound dressing constructed of an ultrathin, semipermeable silicone film with a nylon fabric partially imbedded into the film. The fabric presents to the wound bed a complex 3-D structure of trifilament thread to which porcine dermal collagen has been chemically bound. Blood/sera clot in the nylon matrix, thereby firmly adhering the dressing to the wound until epithelialization occurs. U.S. Pat. No. 4,725,279.

Integra Bilayer Matrix Wound Dressing by Integra LifeSciences Corp.—an advanced wound care device comprised of a porous matrix of cross-linked bovine tendon collagen and glycosaminoglycan and a semi-permeable polysiloxane (silicone) layer.

Laserskin by Fidia Advanced Biopolymers—Lam, P. K. et al; "Development and evaluation of a new composite Laserskin graft", J of Trauma: Injury, Infection and Critical Care. 47, 1999. pp. 918-922.

Oasis Wound Matrix by Healthpoint—A biologically derived extracellular matrix-based wound product that is compatible with human tissue. Unlike other collagen-based wound care materials, OASIS is unique because it is a complex scaffold that provides an optimal environment for a favorable host tissue response, a response characterized by restoration of tissue structure and function.

Glucan II—A smooth gas permeable polymeric layer attached to the mesh matrix.

A highly advanced carbohydrate dressing with Beta-Glucan.

SUMMARY OF THE INVENTION

The present silicone/nylon membrane has been developed for applications on wounds or burns. These applications include, but are not limited to superficial wounds, excised deep and full thickness wounds, donor sites, meshed autograph sites, and specialized wound locations such as the hands, face, and feet.

The present invention produces thin silicone/nylon membranes on flat Teflon™ surfaces. In the previous instantiation, vacuum suction was used to produce pores in the membrane by pulling silicone through the Teflon surface. This method has been abandoned, and the present invention uses a method of creating pores through gravity and friction.

Silicone Technology—The present invention uses a Silicone Dispersion mixed with a 15% Solution of Xylene: Heat Cured Mfg. Part Number V40000. It is a custom mixed product for this use and specifically requested for this application. The preferred supplier is Applied Silicones.

Knitting Technology—The present invention uses a knitting machine with a 13 inch cylinder with 1152 needles. It can knit varying length of tubes.

The boarding process follows the knitting of the tube and controls the final width (and length) of the nylon. The form size used in the boarding process is important. The current form is 15¾ inches wide by 32 inches long. The top of the form is tapered for approximately 2 inches. The boarding chamber is larger and can accommodate a form up to 19 inches wide and 32 inches long. There is a significant advantage over competing technologies with a larger final knitted product, allowing for larger final silicone/nylon membranes.

Fabric can be knitted in custom weaves. The preferred weaves and settings for the machine are detailed in a series of technical guides. The different weaves give the final product varying characteristics and are critical in producing the proper end result.

Thin Film Technology

A process to cure a precision membrane after combining it with nylon on a thin, flat, chemically etched, Teflon™ coated "thin film" plate has been developed and is included below. The plate used to cure the membrane is formed out of a thin (0.004" thick), flexible metal that has been chemically etched to produce the desired thickness and hole pattern.

The plate is coated with a low adhesion Teflon™ coat (Silverstone™). The coating is critical as the membrane will not release properly without it. As noted in the prior art, the Silverstone™ coating is superior to its alternates (White virgin Teflon™ and a standard Teflon™ coating). The plates are cleaned between uses so that no residue is left behind on the final silicone/nylon membrane.

The thin plate design allows for numerous benefits over the prior invention. First, issues with metal plates warping in extreme heat have been eliminated, as the process for developing the new plate does not require such high cure temperatures. Secondly, when placed on the vacuum sub panel as described below, the thin plate can be held extremely flat. As in the prior art, it is absolutely critical that the surface is as flat as possible so as to allow for the silicone dispersion to be layered consistently, flat, and level, with minimal variations in thickness. These two additions in the current invention are superior to prior inventions.

The thin nature of the plate allows for ease of cleaning over prior inventions. The layering process is similar to the process in U.S. patent application Ser. No. 12/326,373. Differences in process are described below.

DETAILED SPECIFICATION

Figure 1:
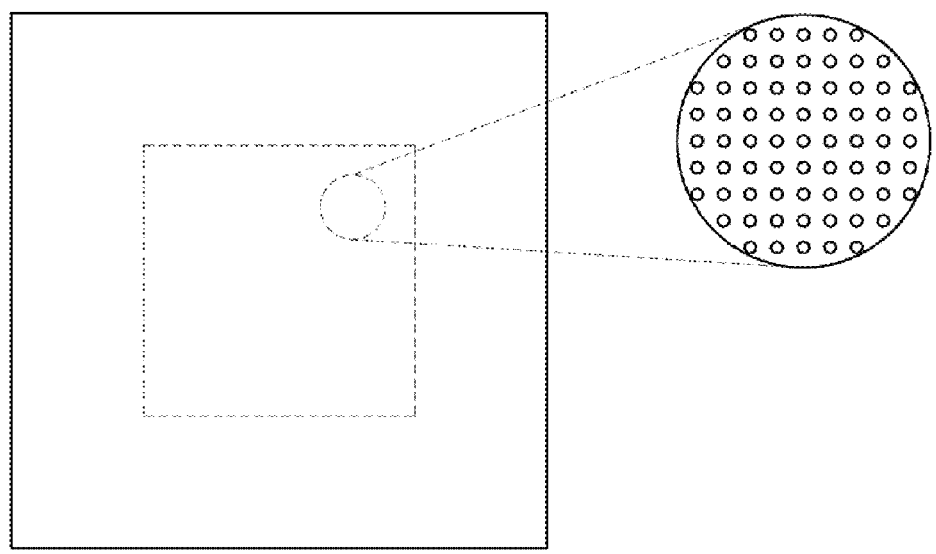
FIG. 1. Typical Thin Film Panel

The skin substitute 100 is comprised of two layers of material, a membrane layer 101 and a nylon weave 102. The membrane layer 101 is fixedly attached to the nylon weave 102 during manufacture. The two layers of the invention are made from non-organic material.

The membrane layer 101 possesses a plurality of pores 103 arranged across its surface in a regular pattern. The pores 103 can be produced in its surface during manufacture by several means, including penetration of the membrane by needles and by means of vacuum suction. The preferred mode is the method described below.

The nylon weave 102 is a produced by a knitting machine with a 13 inch cylinder with 1152 needles. It can knit varying length of tubes of the nylon weave 102.

The nylon weave 102 can be knitted in custom weaves. The preferred weaves and settings for the machine are detailed in an industry standard specification sheet. The different weaves give the skin substitute 100 varying characteristics and are critical in producing the proper end result.

The preferred process to produce the skin substitute 100 is to cure the membrane layer 101 after combining it with nylon weave 102 on a flat surface. The plate 105 used to cure the membrane layer 101 and nylon weave 102 is formed out of an aluminum honey-comb structure with a low density. The low density of the plate 105 gives it low heat sinking properties. The honey-comb like structure allows for a very strong and rigid design, while remaining extremely flat. It is critical that the surface is flat in order to allow the membrane layer 101 to be layered consistently flat, and level, with no variations in thickness.

Figure 2:
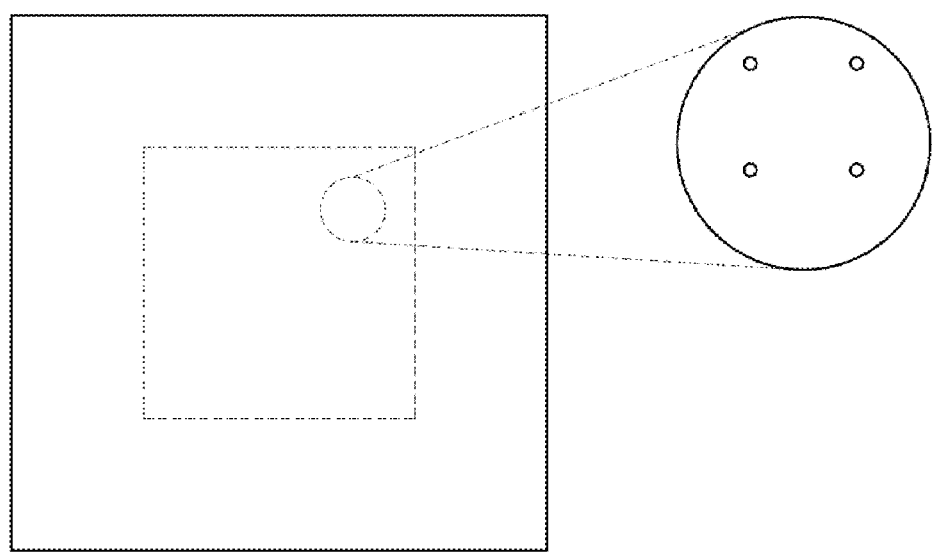
FIG. 2. Sample Sub Panel Layout
Figure 3:
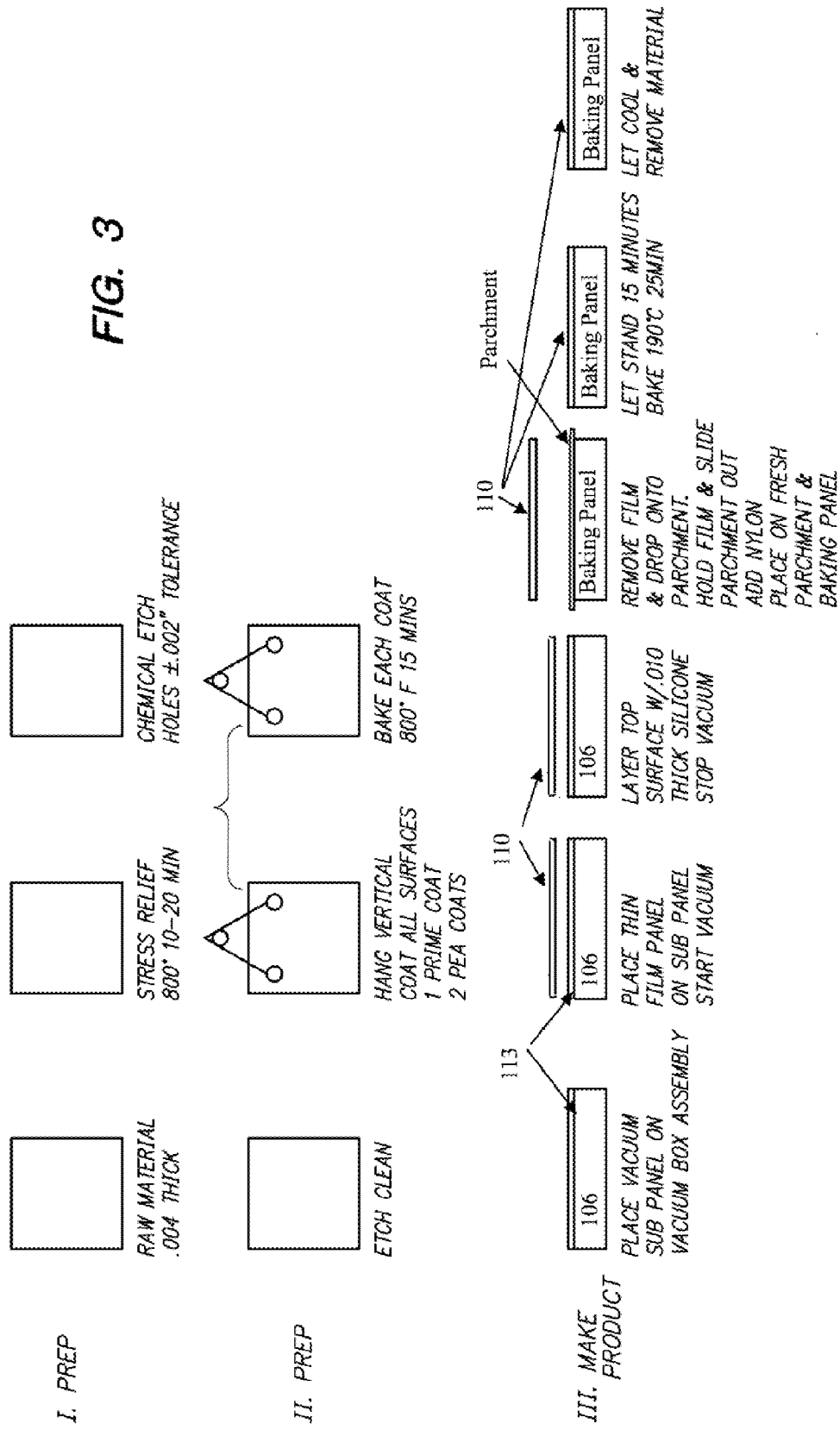
FIG. 3. Process Outline

The preferred embodiment method for making pore holes in the membrane layer 101 involves the use of a thin Teflon™ coated plate, the thin plate 110 as in FIG. 1, with etched holes in combination with a vacuum sub panel 111, as in FIG. 2, to create a thin membrane layer 101.

This method allows removal of portions of the membrane layer 101 at the pore holes in a manner that does not disturb the three-dimensional structure of the knitted nylon attached to the membrane layer 101.

Vacuum Sub Panel

The thin plate 110 is placed over a vacuum subpanel system. The vacuum subpanel system consists of a vacuum box 106 the size of the subpanel plate 113 and the thin plate 110. The vacuum box 106 is sized such that when the subpanel plate 113 is placed on top of it, an airtight seal is created. The side of the vacuum box 106 has an opening where a vacuum or airflow system can be attached. The subpanel plate 113 contains numerous holes in a regular pattern, in the preferred embodiment roughly in the size and position of the holes in the thin plate 110, with larger holes around the border. When the thin plate 110 is placed on top of the subpanel plate 113, it is placed off center, such that the holes in the thin plate 110 and the holes in the subpanel plate 113 do not line up.

When the vacuum system is activated, the thin plate 110 is pulled onto the subpanel plate 113 by air pressure and is not easily moved until the layering process is completed, the silicone membrane 101 is completed on top of the thin plate 110 and the vacuum system is deactivated.

Excess silicone is removed from the upper surface of the silicone membrane 101 via absorbent material. Nylon fabric is applied without wrinkles to the silicone membrane 101. The thin plate 110 with the silicone/nylon membrane on top of it is then lifted and placed on a sheet of absorbent material, in the preferred embodiment parchment paper. The parchment paper is moved under the plate and the excess silicone membrane 101 extruded through the holes in the thin plate 110 rubs off, leaving clear holes in the silicone/nylon membrane. Finally, the thin plate 110 with the nylon and silicone layer is allowed to cure before removal of the porous silicone/nylon membrane.

Results: Over previous technology, the thin plate technology consistently produces higher quality membranes and drastically reduces cleaning time for the thin plate 110 and subpanel plate 113. It generates no debris and allows for greater flexibility in customizing hole/void patterns.

The apparatus and methods described are the preferred and alternate embodiments of this invention, but other methods are possible and are within the contemplation of this patent.

What is claimed is:

1. A skin substitute production means,
the skin substitute comprised of two layers of material, a membrane layer and a nylon weave,
the membrane layer fixedly attached to the nylon weave during manufacture of the skin substitute, the membrane layer and nylon weave made from non-organic material,
the membrane layer possessing a plurality of pores arranged across its surface in a pattern,
the skin substitute production means further comprised of a thin plate and a vacuum box,
the thin plate a rectangular, flat, rigid surface comprised of an aluminum honeycomb structure with a low density, while remaining flat when subjected to 800 degrees Fahrenheit for a period of at least fifteen minutes, the low density of the plate giving it low heat sinking properties,
the thin plate having a plurality of vacuum holes, the vacuum holes drilled through the plate in a characteristic shape, the vacuum holes scattered about the plate in a random pattern, the thin plate covered with a baked-on low adhesion coating,
the low adhesion coating a thin coating that covers the upper surface of the thin plate, the low adhesion coating comprised of a substance that reduces the physical adhesion between the plate and any material placed on it,
the vacuum box a hollow box that when mated with the thin plate makes a vacuum seal, and
means for removing excess material from the membrane layer, wherein the means for removing excess material from the membrane layer is an absorbent material.

2. A skin substitute production means,
the skin substitute comprised of two layers of material, a membrane layer and a nylon weave,
the membrane layer fixedly attached to the nylon weave during manufacture of the skin substitute, the membrane layer and nylon weave made from non-organic material,
the membrane layer possessing a plurality of pores arranged across its surface in a pattern,
the skin substitute production means further comprised of a thin plate, a subplate, and a vacuum box,
the thin plate a rectangular, flat, rigid surface comprised of an aluminum honeycomb structure with a low density, while remaining extremely flat when subjected to 800 degrees Fahrenheit for a period of at least fifteen minutes, the low density of the plate giving it low heat sinking properties,
the thin plate having a plurality of vacuum holes, the vacuum holes drilled through the plate in a characteristic shape, the vacuum holes scattered about the plate in a random pattern, the thin plate covered with a baked-on low adhesion coating,
the subplate a rectangular, flat, rigid surface with a plurality of vacuum holes, the vacuum holes drilled through the plate in a characteristic shape, the vacuum holes scattered about the plate in a random pattern that does not overlap the pattern of the holes in the thin plate,
the low adhesion coating a thin coating that covers the upper surface of the thin plate, the low adhesion coating comprised of a substance that reduces the physical adhesion between the plate and any material placed on it,
the vacuum box a hollow box that when mated with the subplate makes a vacuum seal, and
means for removing excess material from the membrane layer, wherein the means for removing excess material from the membrane layer is an absorbent material.

3. An apparatus, comprising:
a first rectangular plate having a flat and rigid surface containing a plurality of holes arranged across the surface in a first regular pattern, the first rectangular plate being formed with a honey-comb structure having a low density that provides low heat sinking properties, the honey-comb structure further providing strength and rigidity;

a second rectangular plate containing a plurality of holes arranged in a second regular pattern, wherein the holes in the second rectangular plate are formed substantially the same size and formed in the same position as the holes in the first rectangular plate, the second rectangular plate further having larger holes around a border; and a vacuum box sized such that an airtight seal is created when the second rectangular plate is placed on the vacuum box, wherein the first rectangular plate is configured to be placed on top of and off center from the second rectangular plate, such that the holes in the first rectangular plate and the holes in the second rectangular plate do not line up when the first rectangular plate and the second rectangular plate are placed on the vacuum box.

4. The apparatus of claim 3, wherein the surface of the first rectangular plate remains flat when subjected to 800 degrees Fahrenheit for a period of at least fifteen minutes.

5. The apparatus of claim 3, wherein the first rectangular plate is held flat when placed on the second rectangular plate, in order to allow a membrane material to be layered onto the first rectangular plate so that the membrane material is consistently flat and level, without variations in the thickness of the membrane material.

6. The apparatus of claim 5, further including means for removing excess membrane material from the first rectangular plate.

7. The apparatus of claim 6, wherein the means for removing excess membrane material from the first rectangular plate is an absorbent material.

8. The apparatus of claim 7, wherein the absorbent material is parchment paper.

9. The apparatus of claim 8, wherein the membrane material is silicone.

10. The skin substitute production means of claim 1, wherein the absorbent material is parchment paper.

11. The skin substitute production means of claim 10, wherein the membrane material is silicone.

12. The skin substitute production means of claim 2, wherein the absorbent material is parchment paper.

13. The skin substitute production means of claim 12, wherein the membrane material is silicone.

* * * * *

UNITED STATES PATENT AND TRADEMARK OFFICE
CERTIFICATE OF CORRECTION

PATENT NO. : 9,155,820 B2  
APPLICATION NO. : 12/558563  
DATED : October 13, 2015  
INVENTOR(S) : E. Aubrey Woodroof et al.

Page 1 of 1

It is certified that error appears in the above-identified patent and that said Letters Patent is hereby corrected as shown below:

Title Page, Item 63: "Mar. 5, 2008" should be -- Mar. 15, 2008 --.

Signed and Sealed this  
Eighth Day of December, 2015

Michelle K. Lee  
*Director of the United States Patent and Trademark Office*